United States Patent [19]

Summers

[11] Patent Number: 4,850,957
[45] Date of Patent: Jul. 25, 1989

[54] ATHERECTOMY CATHETER
[75] Inventor: David P. Summers, Houston, Tex.
[73] Assignee: American Biomed, Inc., Houston, Tex.
[21] Appl. No.: 143,077
[22] Filed: Jan. 11, 1988
[51] Int. Cl.⁴ .............................................. A61B 17/32
[52] U.S. Cl. ..................................... 604/22; 128/305; 418/48
[58] Field of Search .................. 604/22; 128/304, 305, 128/305.1, 751, 752, 755; 418/48

[56] References Cited
U.S. PATENT DOCUMENTS

| | | |
|---|---|---|
| 3,260,318 | 7/1966 | Neilson et al. |
| 3,760,447 | 9/1973 | Vivion ................... 410/48 |
| 3,930,765 | 1/1976 | Waite ..................... 418/48 |
| 4,273,128 | 6/1981 | Lary . |
| 4,443,165 | 4/1984 | Chanton ............... 418/48 |
| 4,445,509 | 5/1984 | Auth ...................... 128/305 |
| 4,492,276 | 1/1985 | Kamp . |
| 4,631,052 | 12/1986 | Kensey . |
| 4,637,785 | 1/1987 | Bäckström ........... 418/48 |
| 4,650,466 | 3/1987 | Luther . |
| 4,729,763 | 3/1988 | Henrie ................... 128/305 |

OTHER PUBLICATIONS

Plaque attack: Cutters and Borers Headed for Coronaries, May–Jun. 1987, PTCA, vol. II, Issue 3.
New Downhole Motor Develops High Torque for Increased Penetration Rates Jun. 1982, Ocean Industry.

Primary Examiner—Stephen C. Pellegrino
Assistant Examiner—Ralph Lewis
Attorney, Agent, or Firm—Gunn, Lee & Miller

[57] ABSTRACT

An atherectomy catheter is disclosed comprising an outer catheter tube and an inner catheter tube centrally received within the outer catheter tube and defining an annular passage therebetween. A hydraulic motor is housed within the inner catheter tube and includes a cutting element connected to the drive shaft of the hydraulic motor. A guide wire extends in advance of the cutter element for guiding the catheter through an artery or the like. Pressurized fluid drives the hydraulic motor for rotating the cutter element. Fluid and tissue debris is removed from the site of plaque removal via the annular passage.

19 Claims, 1 Drawing Sheet

ATHERECTOMY CATHETER

BACKGROUND OF THE DISCLOSURE

The present invention is directed to an atherectomy catheter, particularly, an atherectomy catheter including a positive displacement drive hydraulic motor.

Many technological advancements have been made in recent years for treatment of coronary disease. Surgical bypass techniques such as cardiopulmonary bypass surgery is routinely performed and is highly successful. While the risks of bypass surgery have been minimized through technological advancements, opening of the chest cavity is required. This requires special surgical skills and equipment which are not readily available in many areas. In many patients, a bypass operation may not be indicated and therefore various surgical techniques have been devised to treat occlusive coronary artery disease of such patients. For example, various prior art devices have been developed for removing and/or compressing atherosclerotic plaque, thromboses, stenoses, occlusions, clots, embolic material, etc. from veins, arteries, and the like. One such device is disclosed in U.S. Pat. No. 4,650,466 (Luther). Luther discloses an angioplasty device comprising a woven tube of metal or plastic fibers and a retraction stylet that are attached at one end of a catheter tube for insertion into a vein, artery and the like for the removal of plaque and similar material. One or more guide wires are attached to the woven tube for rotation and manipulation inside the artery. The woven tube is placed within the artery and expanded to contact the interior, plaque coated wall of the artery. Movement of the expanded woven tube abrades the plaque from the arterial wall to form particles which are trapped within the woven tubes. Removal of the angioplasty device from the artery removes the trapped plaque particles from the patient.

Other prior art devices include catheters fitted with an inflatable balloon for compressing occlusive materials such as plaque against the vessel wall. U.S. Pat. No. 4,273,128 (Lary) discloses a coronary cutting and dilating instrument for treatment of stenotic and occlusive coronary artery disease. The instrument disclosed therein includes a cutting and dilating instrument having one or more radially extending knife blades at a forward end thereof for making the coronary incision and an inflatable balloon for dilating the stenotic artery zone immediately after the incision.

Other angioplasty devices include a catheter having a motor driven cutting head mounted at its distal end. The cutting head is connected to the drive motor via a flexible drive shaft extending through the catheter. Extremely high rotational cutting head speeds have been achieved, in the range of two to three hundred thousand rpm, by these motor driven cutter heads. Various problems, however, have been associated with the use of balloon tipped catheters and high speed cutting heads. The balloon catheter is expanded by injection of pressurized fluid into the balloon to expand it against the wall of the artery. Some problems which have been reported include vessel dissection, perforation, rupture, conversion of a stenosis to an occlusion and embolization. Furthermore, angioplasty devices utilizing balloons do not remove the plaque from the arterial wall but simply compress the plaque against the wall of the vessel. Thus, the stenosis or occlusion frequently reoccur requiring further treatment.

Atherectomy devices utilizing motor driven high speed cutting head include a number of disadvantages. Heat dissipation and vibration is a problem. The path to the occlusion in an artery is often a tortuous path and therefore the flexible drive shaft connected to the cutter head must often traverse a number of bends or curves. Consequently, as the flexible drive shaft rotates, it contacts the inner wall of the catheter resulting in localized heating and vibrations due to the frictional contact. This, of course, is very uncomfortable for the patient and may result in weakening or perforation of the vessel.

It is therefore an object of the invention to provide an atherectomy catheter having a rotary cutter head at the distal end thereof driven by a positive displacement hydraulic motor.

It is another object of the invention to provide an atherectomy catheter having a relatively low speed cutter head powered by a high torque motor.

It is yet another object of the invention to provide an atherectomy catheter including a return passage for evacuating plaque and tissue removed by the cutting element.

SUMMARY OF THE INVENTION

An atherectomy catheter is disclosed for removing plaque, stenosis, occlusions, or the like from an artery or coronary vessel. The catheter comprises a flexible hollow tube housing a positive displacement motor at its distal end. A cutting element is connected to the positive displacement motor and is rotated thereby. The hollow tube is concentrically located within an outer tube, the ends of which are connected to a pump. An annulus or return passage is defined between the inner and outer tubes. The positive displacement motor is driven by pressurized fluid flowing through the inner tube past the drive motor and returning through the return passage defined between the inner and outer tubes to the pump, thereby defining a closed loop hydraulic system. Fluid pressure and velocity is converted into rotary motion to rotate the cutting element.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are, therefore, not to be considered limiting of its scope, for the invention may admit to other equally effective embodiments.

DETAILED DESCRIPTION OF THE PREFERRED EMBODIMENT

Figure 2:
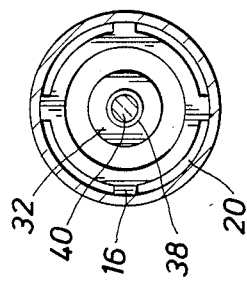
FIG. 2 is a sectional view of the apparatus of the invention taken along lines 2—2 of FIG. 1.
Figure 1:
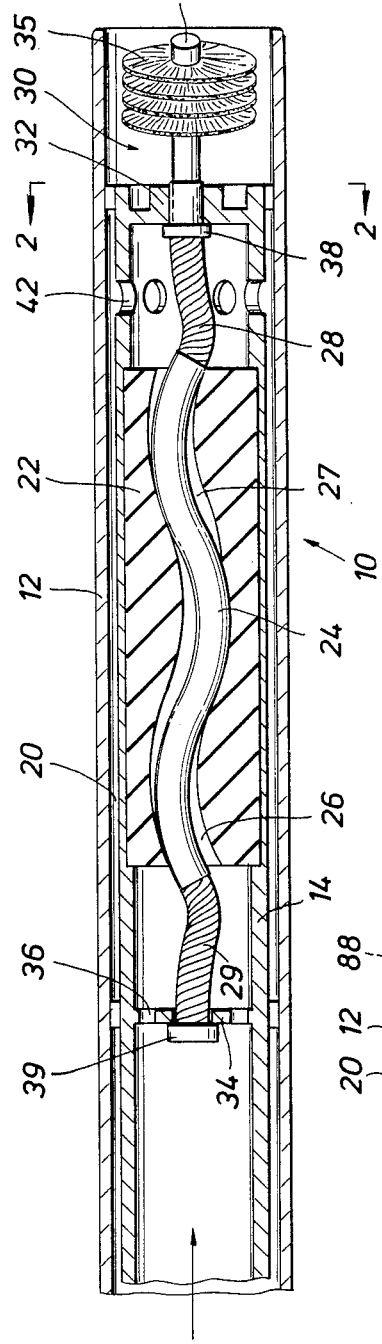
FIG. 1 is a sectional view of the apparatus of the invention.

Referring first to FIG. 1, the catheter of the invention is generally identified by the reference numeral 10. The catheter 10 of the invention comprises a flexible tube 12 which may be several feet in length. Concentrically received within the outer tube 12 is an inner catheter tube 14. The outer hollow tube 12 is spaced from the catheter tube 14 by spacers 16 located along the length of the catheter tube 14 to concentrically locate the catheter tube 14 within the outer tube 12. An annulus or return passage 20 is defined between the outer tube 12 and catheter tube 14. The annulus 20 provides a return passage for fluid and plaque or tissue debris removed from the arterial wall. The spacers 16, as best shown in FIG. 2, are integrally formed ribs on the catheter tube 14. The ribs or spacers 16 concentrically position the cathether tube 14 within the outer tube 12. The spacers 16 divide the annulus 20 into separate return passages as shown in the sectional view of FIG. 2. Alternatively, the spacers 16 may be perforated rings mounted about the catheter tube 14. The rings may be spaced among the length of the catheter tube 14 to maintain the concentric relationship with the outer tube 12. The rings are perforated so as not to interfere with fluid flow through the annulus 20.

The catheter tube 14 is a hollow flexible tube housing a positive displacement motor at its forward end. The motor is hydraulically driven by fluid pressure applied through the catheter tube 14. The motor includes a stator 22 and rotor 24. The stator 22 may be formed of elastomer material and the rotor 24 may be a polished steel rod. The stator 22 defines a cavity 26 which supports and guides the rotor 24. The cavity 26 is uniformly curved in a spiral-like helical shape. The rotor 24 includes a similar spiral-like helical configuration. The dissimilarity of shape between the stator 22 and rotor 24 creates wedge shaped cavities 27 within the cavity 26. Fluid under pressure forced into the stator cavity 26 provides the power to turn or rotate the rotor 24. The fluid seeks an exit through the stator cavity 26 and wedge shaped cavities 27. It will be observed that the rotor 24 contacts the stator 22 at several points along its length. The elastomer stator 22 is resilient and forms a positive seal against the rotor 24 at the points of contact. Little or no fluid may pass through this seal. The fluid exerts a force against the rotor 24 and thereby turns the rotor 24 within the stator 22. Thus, the motor of the invention has a positive displacement. That is, a given volume of fluid passing through the stator cavity 26 and exiting through the ports 42 of the catheter tube 14 will always turn the rotor 24 the same number of degrees. Rotor speed increases directly with the increase in the volume of fluid forced through the stator 22.

The rotor 24 moves radially within the stator 22 as it rotates. Thus, the ends of the rotor 24 move in an eccentric motion. To compensate for the angular misalignment of the eccentric motion of the rotor 24, flexible universal joints 28 and 29 are bonded to the ends of the rotor 24. The flexible universal joints 28 and 29 translate the eccentric motion of the rotor 24 to a rotary motion for rotating a cutting element 30 connected to the universal joint 28 at the forward end of the rotor 24. The universal joints 28 and 29 are supported concentrically within the catheter tube 14 by support plates 32 and 34. The support plate 32 supports the distal end of the universal joint 28. The support plate 34 includes a plurality of apertures 36 permitting fluid to enter the stator cavity 26.

The support plate 32 provides a closure for the forward end of the motor housing. The plate 32 includes a centrally located opening for receiving an end of the flexible universal joint 28 therethrough. Thrust bearings 38 journaled about the universal joints 28 and 29 are supported by the support plates 32 and 34 permitting the rotor 24 to rotate freely and minimize binding.

Figure 4:
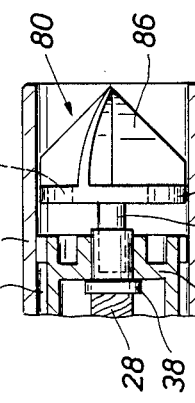
FIG. 4 is a partial sectional view of a cutting element for use with the apparatus of the invention.

The cutting element 30 may comprise a number of different cutting heads which are interchangeable. An alternate cutting head 80 is shown in FIG. 4. In the embodiment shown in FIG. 1, the cutting element 30 comprises a plurality of continuous filament brush cutters 35 mounted about a shaft 40. In the retracted position shown in FIG. 1, the cutting element 30 is housed within the forward end of the outer tube 12. The catheter tube 14 and outer tube 12 telescope relative to each other. The cutting element 30 is exposed for removing plaque from the arterial wall by advancing the inner catheter tube 14 forward to expose the cutting element 30. Plaque is removed from the arterial wall and swept back behind the cutters 35 and removed through the annulus 20.

Figure 3:
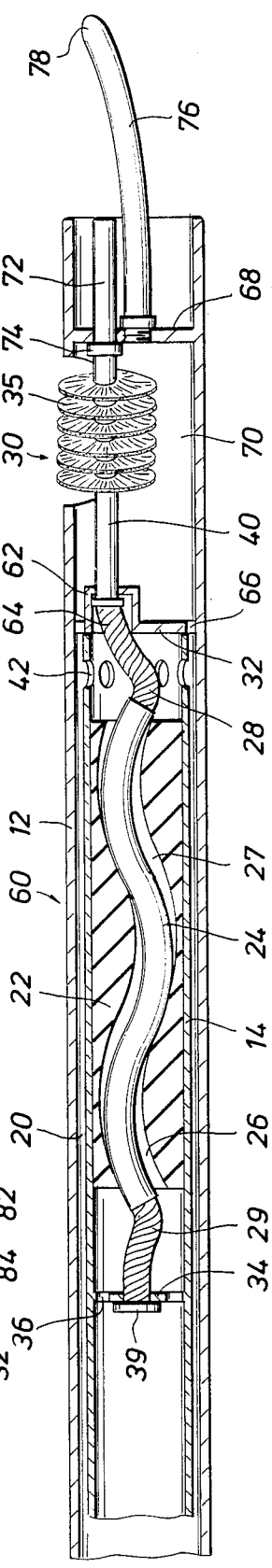
FIG. 3 is an alternate embodiment of the apparatus of the invention.

Referring now to FIG. 3, an alternate embodiment of the invention is disclosed. The catheter 60 shown in FIG. 3 is substantially similar to the catheter 10 of FIG. 1 and therefore like reference numerals are used to identify like elements of the catheters. The catheter 60 includes a flexible outer tube 12 and an inner catheter tube 14 concentrically received within the outer tube 12. The hydraulically driven positive displacement motor comprising the stator 22 and rotor 24 is housed within the inner catheter tube 14 at the forward end and operates in the same manner described above with regard to FIG. 1.

The catheter 60 is particularly suitable for removal of plaque or other occlusive material from a specific area in an artery. In some instances, for example calcific lesions, the calcified material may only partially block one side of an artery so that a 360° sweep of the arterial wall is not required. To this end, the catheter 60 is provided with a cutter element cavity or chamber 70 which substantially encloses the cutter element 30. The chamber 70 is provided with a slot or window so that only a portion of the cutting element 30 is exposed when in the cutting position. The cutting window permits the cutting element 30 to sweep the arterial wall in an arc of 150° to 180° and thereby remove the occlusive material partially blocking the artery. The back exterior surface of the chamber 70 rests against the arterial wall opposite the lesion so that the cutting element 30 is braced for cutting the calcified lesion. Motor driven high speed cutter blades tend to bounce off calcified lesions which may result in perforation of the arterial wall. The cutting window of the catheter 60 partially shrouds and braces the cutting element 30 so that it does not bounce off the lesion. Thereby, the calcific lesion may be removed without perforation of the arterial wall. The cutting window may, of course, be increased or decreased in size thereby exposing more or less of the cutting element 30 for removing the occlusive material.

It will be observed that the shaft 40 carrying the cutting element 30 is elongated and provided with an extension 72. The shaft 40 is supported at opposite ends by support plates 32 and 68. The support plate 32 is provided with a shaft hub 62. The shaft hub 62 defines a cavity 64 which is enlarged relative to the diameter of the shaft 40 and the universal joint 28 to accommodate for the eccentric motion of the rotor 24. An enlarged portion 74 on the shaft 40 provides a stop shoulder for engaging the support plate 68 and thereby limiting the forward advancement of the cutting element 30 within the chamber 70. The stop 74 centrally positions the cutting element within the cutting window upon contacting the support plate 68.

The shaft 40 may be advanced in a forward or backward direction within the chamber 70. This is accomplished by advancing or retracting the inner catheter 14. The inner catheter 14 may be retracted to retract the cutter element 30 so that the cutters 35 are totally enclosed within the chamber 70. This is particularly advantageous in that the cutters 35 are not exposed while the catheter 60 is advanced through the artery to the area of the occlusion. Once the occlusion has been reached, the catheter 60 is oriented so that the cutting window faces the occlusion or obstruction. The inner catheter 14 is pushed forward to position the cutting element 30 so that the cutters 35 are exposed within the cutting window for cutting away the occlusive material. The cutters 35 are flexible so that when the cutting element 30 is retracted, the cutters 35 bend slightly to fit within the outer tube 12. In the cutting position, the cutters 35 extend slightly beyond the outer diameter of the outer tube 12. The extension 72 is of sufficient length so that it does not disengage from the support plate 68 upon retraction of the cutting element 30 so that it is stored within the outer tube 12.

The catheter 60 includes a blunt guide wire 76 having a slightly angularly displaced tip 78. The guide wire 76 is threadably mounted to the support plate 68 and is centrally located thereon. The guide wire 76 aides in properly positioning the catheter 60 within an artery or vessel. The angularly displaced tip 78 permits the cather 60 to be oriented and to follow a particular branch in a vessel to the occluded area of the vessel.

Referring now to FIG. 4, an alternate embodiment of a cutter head which may be utilized with the catheter of the invention is disclosed. The cutting element 80 comprises a circular base 82 sized to fit within the outer tube 12. A shaft 84 connects the cutting element 80 to the flexible universal joint 28. The cutting element 80 includes a plurality of cutting blades 86 which project forwardly from the base 82. The base 82 and the blades 86 may be integrally formed from a single piece of stock material, such as stainless steel. The cutting blades 86 converge inwardly from the periphery of the base 82 to a point defining the rotational axis of the cutting element 80. The blades 86 are slightly curved so that plaque or occlusive material removed by the cutting element 80 is swept back toward the base 82 and through openings 88 in the base 82 for removal through the annulus 20. The cutting element 80 is particularly useful for removal of heavily calcified lesions and substantially total occlusions in an artery or the like.

The catheters 10 and 60 of the invention may both be utilized to remove plaque or blockages from vessels or arteries in the human body as previously described. For purposes of illustration, however, the following discussion will be directed to the use of the catheter 10 in removing plaque deposits from a coronary artery. To this end, the catheter 10 is introduced into the body of the patient through a femoral artery or some other artery selected by the physician. The catheter is pushed through the femoral artery to the site in the coronary artery requiring removal of plaque. Fluid pressure is applied to the catheter 10. The fluid exerts a force against the rotor 24. The fluid force turns the rotor 24 and thereby turns the cutting element 30 connected to the rotor 24 via the flexible universal joint 28. Rotation of the cutting element 30 cuts or scrapes the plaque from the vessel wall. The cutting element sweeps the removed plaque into the catheter cavity where it is removed through the annulus 20 by suction applied by a vacuum pump (not shown in the drawings) connected to the catheter 10. Sufficient torque is developed by the hydraulic motor so that the cutting element 30 does not stall when contacting the plaque on the walls of the vessel. Pressure is applied to the catheter 10 to force the cutting element 30 against the plaque so that the cutting element blades 35 remove bits of the plaque on each rotation. It is understood that the cutting element 30 has a sweep diameter slightly less than the diameter of the coronary artery so that the arterial wall is not cut or perforated. Upon removal of the plaque or obstruction, the catheter 10 is removed from the artery and the surgical incisions on the patient are closed.

While the foregoing is directed to the preferred embodiments of the present invention, other and further embodiments of the invention may be devised without departing from the basic scope thereof, and the scope thereof is determined by the claims which follow.

What is claimed is:

1. An atherectomy catheter for removal of occlusive material in an artery, comprising:
   (a) an outer catheter tube;
   (b) an inner catheter tube concentrically received within said outer catheter tube and defining an annulus therebetween;
   (c) a hydraulic motor housed within said inner catheter tube, wherein said hydraulic motor comprises a stator and rotor means, said stator defining a cavity which supports and guides said rotor means and wherein said cavity is uniformly curved in a spiral-like helical shape;
   (d) cutting means connected to said hydraulic motor;
   (e) guide means extending in advance of said cutting means for guiding the catheter through the artery; and
   (f) pump means for pumping fluid through the catheter for driving said hydraulic motor and creating a vacuum for removing fluid and occlusive material through said annulus.

2. The apparatus of claim 1 wherein said rotor means comprises a rotor formed in a spiral-like helical configuration.

3. The apparatus of claim 2 wherein pressurized fluid forced through said cavity provides power for rotating said rotor.

4. The apparatus of claim 3 wherein said rotor includes flexible universal joints bonded at each end thereof for translating the eccentric motion of said rotor to a rotary motion for rotating said cutting means.

5. The apparatus of claim 4 including bearing means journaled about said universal joints supported by support plate means mounted within said inner catheter tube.

6. The apparatus of claim 5 wherein said inner catheter tube includes a plurality of ports permitting fluid to exit therethrough into said annulus.

7. The apparatus of claim 6 wherein said cutting means comprises a cutter element formed of continuous filament fibers defining a brush-like cutter.

8. The apparatus of claim 1 wherein fluid pressure for driving said hydraulic motor is provided by water forced through said innner catheter tube by said pump means.

9. The apparatus of claim 1 wherein said cutting means comprises a plurality of curved cutting blades for sweeping bits of occlusive material into said inner catheter tube for removal via said annulus.

10. The apparatus of claim 1 wherein said outer catheter tube includes a chamber for housing said cutting means, said chamber having a window opening providing access to the occlusive material by said cutting means.

11. The apparatus of claim 10 wherein said window opening permits said cutting means to contact the occlusive material through an arc of 150° to 180°.

12. The apparatus of claim 10 wherein said cutting means is retractable to a storage position within said chamber.

13. The apparatus of claim 10 wherein said cutting means includes a drive shaft reciprocally supported on support plate means mounted within said outer catheter tube.

14. An apparatus for removing an obstruction in a vessel in the human body, comprising:
   (a) an outer catheter tube;
   (b) an inner catheter tube concentrically received within said outer catheter tube and defining an annulus therebetween;
   (c) a hydraulic motor housed within said inner catheter tube, wherein said hydraulic motor includes a stator and rotor means, said stator defining a cavity uniformly curved in a spiral-like helical shape for supporting and guiding said rotor means;
   (d) cutting means connected to said hydraulic motor; and
   (e) pump means for pumping fluid through the catheter for driving said hydraulic motor and creating a vacuum for removing fluid and bits of obstruction through said annulus.

15. The apparatus of claim 14, wherein said rotor means comprises a rotor formed in a spiral-like helical configuration corresponding to the spiral-like helical shape of said cavity defined by said stator.

16. The apparatus of claim 15 wherein said rotor includes flexible universal joints bonded at each end thereof for translating the eccentric motion of said rotor to a rotary motion for rotating said cutting means.

17. The apparatus of claim 16 including bearing means journalled about said universal joints supported by support plate means mounted within said inner catheter tube.

18. The apparatus of claim 17 wherein said cutting means comprises a cutter element formed of continuous filament fibers defining a brush-like cutter.

19. The apparatus of claim 14 wherein said cutting means comprises a plurality of curved cutting blades mounted on a circular base mounted to one of said universal joints, wherein said cutting blades project inwardly from the periphery of said circular base to a point defining the rotational axis of said cutting means.

* * * * *